United States Patent
Fei et al.

(10) Patent No.: US 9,795,548 B2
(45) Date of Patent: Oct. 24, 2017

(54) ORAL CARE COMPOSITIONS

(75) Inventors: Lin Fei, Kendall Park, NJ (US); Ying Yang, Monmouth Junction, NJ (US); Stanistav Jaracz, Somerset, NJ (US); Geofeng Xu, Plainsboro, NJ (US)

(73) Assignee: Colgate-Palmolive Company NY (US)

( * ) Notice: Subject to any disclaimer, the term of this patent is extended or adjusted under 35 U.S.C. 154(b) by 0 days.

(21) Appl. No.: 14/381,024

(22) PCT Filed: Mar. 2, 2012

(86) PCT No.: PCT/US2012/027523
§ 371 (c)(1),
(2), (4) Date: Aug. 26, 2014

(87) PCT Pub. No.: WO2013/130104
PCT Pub. Date: Sep. 6, 2013

(65) Prior Publication Data
US 2015/0004104 A1    Jan. 1, 2015

(51) Int. Cl.
*A61K 36/575* (2006.01)
*A61Q 11/00* (2006.01)
*A61K 8/34* (2006.01)
*A61K 8/37* (2006.01)
*A01N 31/08* (2006.01)

(52) U.S. Cl.
CPC .............. *A61K 8/345* (2013.01); *A01N 31/08* (2013.01); *A61K 8/347* (2013.01); *A61K 8/375* (2013.01); *A61K 36/575* (2013.01); *A61Q 11/00* (2013.01); *A61K 2800/49* (2013.01)

(58) Field of Classification Search
CPC .............................. A61K 36/575; A61Q 11/00
See application file for complete search history.

(56) References Cited

U.S. PATENT DOCUMENTS 5,019,373 A * 5/1991 Carter .................... A61Q 11/00
424/49

FOREIGN PATENT DOCUMENTS

| IN | WO 2010092596 A1 * | 8/2010 | ........... A61K 9/1075 |
|---|---|---|---|
| JP | 07033649 A * | 2/1995 | |
| JP | H7-33649 | 2/1995 | |
| WO | WO 9804234 A1 * | 2/1998 | ............... A61K 8/02 |
| WO | WO 2011/106492 | 9/2011 | |
| WO | WO 2011/106493 | 9/2011 | |
| WO | WO 2011/131436 | 10/2011 | |

OTHER PUBLICATIONS

International Search Report and the Written Opinion issued in International Application PCT/US2012/27523 mailed Dec. 13, 2012 WO.
Written Opinion of the International Preliminary Examining Authority issued in International Application PCT/US2012/27523 mailed Mar. 3, 2014 WO.
Alexakis et al., 2004, "Biphenol-based phosphoramidite ligands for the enantioselective copper-catalyzed conjugate addition of diethylzinc," J. Org. Chem. 69:5660-5667.
Griffin, 1949, "Classification of Surface-Active Agents by 'HLB,'" Journal of Cosmetic Science 1(5):311-326.

* cited by examiner

*Primary Examiner* — Tracy Liu

(57) ABSTRACT

Described herein are compositions comprising isopropyl magnolol; a surfactant system; and an orally acceptable carrier, together with methods of making and using the same.

6 Claims, No Drawings

ORAL CARE COMPOSITIONS

BACKGROUND

There is a need for safe and effective antibacterial and anti-inflammatory agents for use in oral care compositions. Magnolol and derivatives thereof have demonstrated efficacy against oral pathogens.

However, the solubility some of these derivatives, e.g., isopropyl magnolol both in water and in oil, and its strong tendency to crystallize out from the composition matrix in a variety of surfactant systems limit its antibacterial potential and disfavor its use in oral care formulations. There is a need for oral care compositions that are both orally acceptable and capable of solubilizing isopropyl magnolol.

SUMMARY

In some embodiments, the present invention provides oral care compositions comprising: isopropyl magnolol; a surfactant system; and an orally acceptable carrier. In some embodiments, the surfactant system comprises a co-surfactant.

Some embodiments of the present invention provide the use of any of the compositions described herein for treating a disease or condition of the oral cavity.

Other embodiments provide methods of treating an oral condition of the oral cavity, comprising administering any one of the compositions described herein, to the oral cavity of a subject in need thereof.

The present inventors surprisingly discovered that adding a particular co-surfactant(s), e.g., propylene glycol monocaprylate (PGC) (also known as propylene glycol monooctanoate and 1,2-propanediol monocaprylate); to a composition comprising isopropyl magnolol greatly enhances its solubility in the composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

Some embodiments of the present invention provide oral care compositions comprising: isopropyl magnolol; a surfactant system; and an orally acceptable carrier.

In some embodiments, the surfactant system comprises a co-surfactant.

As used herein, the term "co-surfactant" means an agent which is used to increase the solubilizing capacity of a surfactant system.

As used herein, the term "solubilizing effective amount" refers to the amount of an ingredient effective to sufficiently solubilize the amount of isopropyl magnolol present in an orally acceptable carrier.

In some embodiments, the co-surfactant has an HLB value of about 10. In some embodiments, the co-surfactant has an HLB value of less than 10. In some embodiments, the co-surfactant has an HLB value of from about 1 to about 9. In some embodiments, the co-surfactant has an HLB value of from about 2 to about 8. In some embodiments, the co-surfactant has an HLB value of from about 3 to about 7. In some embodiments, the co-surfactant has an HLB value of from about 3 to about 10. In some embodiments, the co-surfactant has an HLB value of from about 4 to about 8. In some embodiments, the co-surfactant has an HLB value of 5 or 6. In some embodiments, the co-surfactant has an HLB value of about 5. In some embodiments, the co-surfactant has an HLB value of 5. In other embodiments, the co-surfactant has an HLB value of about 6. In other embodiments, the co-surfactant has an HLB value of 6.

As used herein, the term "HLB" refers to hydrophilic-lipophilic balance of a component and is a measure of the degree to which it is hydrophilic or lipophilic, determined by calculating values for the different regions of the molecule, as described by Griffin (see, e.g., Classification of Surface-Active Agents by 'HLB,'" *Journal of the Society of Cosmetic Chemists* 1 (1949): 311).

In some embodiments, the co-surfactant is present in an amount sufficient to solubilize the isopropyl magnolol in the orally acceptable carrier. In some embodiments, the co-surfactant is a monoester of propylene glycol. In other embodiments, the monoester of propylene glycol is selected from propylene glycol monocaprylate and propylene glycol monolaurate. In some embodiments, the co-surfactant is propylene glycol monocaprylate.

In some embodiments, the surfactant system further comprises a surfactant having an HLB value greater than 10. In some embodiments, the surfactant having an HLB value greater than 10 includes, but is not limited to, sodium lauryl sulfate, a polysorbate, a betaine surfactant. In some embodiments, the surfactant having an HLB value greater than 10 is sodium lauryl sulfate.

In some embodiments, the surfactant having an HLB value greater than 10 is present in an amount from about 0.01 to about 3%, by weight, of the composition. In some embodiments, the surfactant having an HLB value greater than 10 is present in an amount from about 0.1 to about 2.5%, by weight, of the composition. In some embodiments, the surfactant having an HLB value greater than 10 is present in an amount from about 0.5 to about 2.2%, by weight, of the composition. In some embodiments, the surfactant having an HLB value greater than 10 is present in an amount from about 1 to about 2%, by weight, of the composition. In some embodiments, the surfactant having an HLB value greater than 10 is present in an amount from about 1.5 to about 1.9%, by weight, of the composition. In some embodiments, the surfactant having an HLB value greater than 10 is present in an amount of about 2%, by weight, of the composition. In some embodiments, the surfactant having an HLB value greater than 10 is present in an amount of about 1.8%, by weight, of the composition.

In further embodiments, the isopropyl magnolol is present in an antibacterially effective amount. In some embodiments, the isopropyl magnolol is present in the amount of about 0.001 to about 10%, by weight, of the composition. In some embodiments, the isopropyl magnolol is present in the amount of about 0.005 to about 9.5%, by weight, of the composition. In some embodiments, the isopropyl magnolol is present in the amount of about 0.01 to about 9%, by weight, of the composition. In some embodiments, the isopropyl magnolol is present in the amount of about 0.05 to about 7.5%, by weight, of the composition. In some embodiments, the isopropyl magnolol is present in the amount of about 0.1 to about 5%, by weight, of the composition. In some embodiments, the isopropyl magnolol is present in the amount of about 0.2 to about 3%, by weight, of the composition. In some embodiments, the isopropyl magnolol is present in the amount of about 0.25 to about 2%, by weight, of the composition. In some embodiments, the isopropyl magnolol is present in the amount of about 0.3 to about 1.5%, by weight, of the composition. In some embodiments, the isopropyl magnolol is present in the amount of about 0.4 to about 1.2%, by weight, of the composition. In some embodiments, the isopropyl magnolol is present in the amount of about 0.5 to about 1%, by weight, of the composition. In some embodiments, the isopropyl magnolol is present in the amount of about 0.5%, 0.7%, or 1%, by weight, of the composition. In some embodiments, the isopropyl magnolol is present in the amount of from about 0.1% to about 3%, by weight, of the composition.

In some embodiments, the ratio by weight of isopropyl magnolol to the co-surfactant is from about 0.1:1 to about 2:1. In some embodiments, the ratio by weight of isopropyl magnolol to the co-surfactant is from about 0.3:1 to about 1.5:1. In some embodiments, the ratio by weight of isopropyl magnolol to the co-surfactant is from about 0.5:1 to about 1.2:1. In some embodiments, the ratio by weight of isopropyl magnolol to the co-surfactant is from about 0.7:1 to about 1:1. In some embodiments, the ratio by weight of isopropyl magnolol to the co-surfactant is about 0.3:1. In some embodiments, the ratio by weight of isopropyl magnolol to the co-surfactant is about 0.5:1. In some embodiments, the ratio by weight of isopropyl magnolol to the co-surfactant is about 0.7:1. In some embodiments, the ratio by weight of isopropyl magnolol to the co-surfactant is about 1:1. In some embodiments, the ratio by weight of isopropyl magnolol to the co-surfactant is 0.3:1. In some embodiments, the ratio by weight of isopropyl magnolol to the co-surfactant is about 0.5:1. In some embodiments, the ratio by weight of isopropyl magnolol to the co-surfactant is about 0.7:1. In some embodiments, the ratio by weight of isopropyl magnolol to the co-surfactant is about 1:1.

Some embodiments provide for the use of a composition according to any embodiment described herein, for treating a disease or condition of the oral cavity. In some embodiments, the disease or condition of the oral cavity is selected from caries, gingivitis, periodontitis, tooth yellowing and halitosis.

Other embodiments provide methods of treating an oral condition of the oral cavity, comprising administering a composition according to any one of the embodiments described herein, to the oral cavity of a subject in need thereof.

In a certain embodiment, the invention provides an oral care composition (Composition 1), for example a toothpaste, comprising isopropyl magnolol and PGM. For example, the invention provides oral care compositions as follows:

1.1. Composition 1 in the form of a toothpaste;
1.2. Composition 1 in the form of a mouthrinse;
1.3. Any of the foregoing compositions wherein the isopropyl magnolol is present in an antibacterially effective concentration;
1.4. Any of the foregoing compositions comprising an antibacterially effective amount of isopropyl magnolol and an amount of propylene glycol caprylate effective to solubilize the isopropyl magnolol in an orally acceptable carrier;
1.5. Any of the foregoing compositions wherein the concentration of isopropyl magnolol is from 0.1-3%, e.g., about 1-2%, based on the total weight of the composition;
1.6. Any of the foregoing compositions wherein the ratio by weight of isopropyl magnolol to propylene glycol caprylate is from 0.1:1 to 2:1, e.g., about 0.5:1;
1.7. Any of the foregoing compositions further comprising polyethylene glycol, e.g., PEG 600, e.g., in an amount of 0.5-5% by weight, e.g., in a ratio of about 3:1 to about 30:1 relative to the isopropyl magnolol;
1.8. Any of the foregoing compositions further comprising a humectant, e.g., glycerin, sorbitol, or mixtures thereof, e.g., in an amount by weight of about 30%-70%, e.g., 30-60%, e.g., about 35%;
1.9. Any of the foregoing compositions further comprising an anionic surfactant, e.g., sodium lauryl sulfate, e.g., in an amount of 0.5-5%, e.g., about 2%;
1.10. Any of the foregoing compositions further comprising an effective amount of a fluoride ion source, e.g., sodium fluoride, e.g., in an amount by weight of 0.1-0.5%, e.g., about 0.24%;
1.11. Any of the foregoing compositions further comprising flavoring, e.g., selected from non-caloric sweeteners, e.g., saccharine, herbal flavorings (e.g., mint flavor), and combinations thereof;
1.12. Any of the foregoing compositions further comprising an abrasive material, e.g., silica abrasive, precipitated calcium carbonate, or combinations thereof;
1.13. Any of the foregoing compositions comprising the following ingredients:

| Ingredient | % w/w |
| --- | --- |
| PEG600 | 1-4%, e.g., about 3% |
| Flavor | 0-3%, e.g., about 1% |
| Isopropyl magnolol | 0.5-3%, e.g., about 0.5% |
| Propylene glycol monocaprylate (PGC) | 0.5-3%, e.g., about 1% |
| Glycerin | 10-30%, e.g., about 18% |
| Sorbitol | 10-30%, e.g., about 18% |
| Sodium Saccharin | 0.1-0.7%, e.g., about 0.3% |
| Sodium Fluoride | 0.1-0.7%, e.g., about 0.24 |
| Sodium lauryl sulfate (SLS) | 1-3%, e.g., about 1.8% |
| Water | As required for suitable consistency, e.g., about 22-88% |
| Abrasive silica | 0-30%, e.g., about 22% |
| Xanthan gum | 0.1-1.0%, e.g., about 0.4% |
| Sodium carboxymethyl cellulose | 0.1-5%, e.g.., about 1% |
| Titanium dioxide | 0.1 1.0%, e.g., about 0.5% |

1.14. A composition obtained or obtainable by combining the ingredients as set forth in any of the preceding compositions.
1.15. Any of the preceding compositions in a form selected from mouthrinse, toothpaste, tooth gel, tooth powder, non-abrasive gel, mousse, foam, mouth spray, lozenge, oral tablet, dental implement, and pet care product.

In further embodiments, the invention provides a method of treatment, prophylaxis or control of a disease or condition of the oral cavity, for example a bacterial infection or inflammatory condition in the mouth, for example gingivitis, comprising applying an oral care composition in accordance with the invention, e.g., Composition 1, et seq., to the oral cavity of a patient in need thereof. In some embodiments, the disease or condition of the oral cavity includes a disease or condition of the teeth, oral mucosa, gingiva or tongue. Such diseases or conditions include caries, gingivitis, periodontitis, and cosmetic conditions such as yellowing and malodor.

In a further embodiment, the invention provides the use of isopropyl magnolol and propylene glycol caprylate in combination for the manufacture of an oral care composition, e.g., according to Composition 1 et seq., for such a method of treatment, prophylaxis or control of a disease or condition of the oral cavity.

In some embodiments, the compounds and compositions of the present invention can be prepared generally according to methods known to those skilled in the art, for example, those reported by Alexakis (Alexakis et al., *J. Org. Chem.* 69: 5660-5667 (2004)).

In further embodiments, the invention provides a method of making an oral care composition, e.g., according to Composition 1, et seq., comprising admixing propylene glycol caprylate and isopropyl magnolol with an orally acceptable carrier.

The methods and compositions of the present embodiments impart advantages over the prior art compositions by providing an oral composition that is well solubilized, safe, and highly efficacious against bacterial infection and/or inflammation in a mammalian subject.

In some embodiments, the composition further comprises an active compound selected from: magnolol, tetrahydromagnolol, butyl magnolol, honokiol, tetrahydrohonokiol, triclosan, delmopinol, cetyl pyridinium chloride, a zinc ion source, a stannous ion source, an anti-inflammatory agent, a botanical agent, and a combination of two or more thereof.

Magnolol (5,5'-Diallyl-biphenyl-2,2'-diol) is a bioactive compound found in the bark of the Houpu magnolia (*Magnolia officinalis*). Isopropyl magnolol (5,5'-diisopropyl-2,2'-dihydroxy biphenol) is a synthetic analog of magnolol, with antibacterial and anti-inflammatory properties, having a structure as follows:

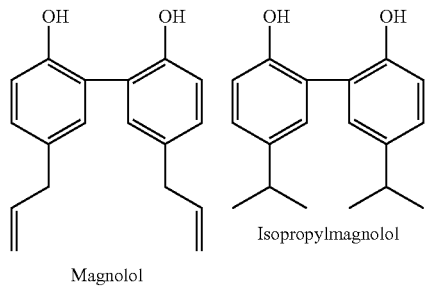

Magnolol    Isopropylmagnolol

As used herein, the term "orally acceptable" means safe for use in the mouth at levels required. In general, all components of the compositions of the present invention are orally acceptable.

The expressions "carrier" or "aqueous carrier" or "orally acceptable carrier" as used throughout this description denote any safe and effective materials for use herein. Such materials include, water, solvents, etc., that may contain a humectant such as glycerin, sorbitol, xylitol and the like. The carrier or orally acceptable carrier also may include additional dentifrice components, such as thickening agents, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

Orally acceptable carriers for use in the invention include the conventional and known carriers used in making toothpastes, tooth powders, prophylaxis pastes, mouth rinses, lozenges, gums, beads, and the like, and are more fully described hereinafter. It is preferred that the orally acceptable carrier does not cause irritation, swelling or pain and does not typically produce an allergic or untoward reaction such as gastric upset, nausea or dizziness. Selection of specific carrier components is dependent on the desired product form, including dentifrices, toothpastes, tooth powders, prophylaxis pastes, mouth rinses, lozenges, gums, gels, paints, confectionaries, and the like.

The term "mouthrinse" in the present invention refers to oral compositions that are substantially liquid in character, such as a mouth wash, spray, or rinse. In such a preparation the orally acceptable carrier typically has an aqueous phase comprising water or a water and alcohol mixture. Further, in various embodiments, the oral carrier includes a humectant and surfactant as described below. Generally, the weight ratio of water to alcohol is in the range of in an amount of 1:1 to 20:1, preferably 3:1 to 10:1 and more preferably 4:1 to 6:1. The total amount of water-alcohol mixture in this type of preparation is typically in an amount of 70 to 99.9% of the preparation. In various embodiments, the alcohol is typically ethanol or isopropanol.

As recognized by one of skill in the art, the orally acceptable carrier of the present invention may also comprise a variety of other conventional active ingredients known to one of skill in the art, including anti-plaque agents, whitening agents, antibacterial agents, tartar control (anticalculus) agent, anti-caries agents, sensitivity agents, and the like. Preferably, the carrier does not substantially reduce the efficacy of the isopropyl magnolol.

The pH of such liquid and other preparations of the oral composition of the present invention is generally between 4.5 to 10. The pH can be controlled with acid (e.g., citric acid or acetic acid) or base (e.g., sodium hydroxide) or buffered (with sodium citrate, acetate, carbonate, or bicarbonate, disodium hydrogen phosphate, or sodium dihydrogen phosphate, for example).

In various embodiments, the aqueous oral composition (e.g., mouthrinse) contains a humectant. The humectant is generally a mixture of humectants, such as glycerin and sorbitol, and a polyhydric alcohol such as hexylene glycol, or polyethylene glycol, although the use of polyethylene glycol as a humectant in addition to its use to enhance the solubility of the active ingredient is optional. The humectant content for a mouth rinse typically is in the range of 5 to 40% and preferably 10 to 30%.

Surfactants suitable for compositions of the present invention include anionic, nonionic, and zwitterionic surfactants. The surfactant usually is present in the aqueous oral compositions of the present invention in an amount of 0.01% to 5%, preferably in an amount of 0.5% to 2.5%.

The oral composition according to the present invention may optionally include other materials, such as for example, cleaning agents, flavouring agents, sweetening agents, adhesion agents, surfactants, foam modulators, abrasives, pH modifying agents, humectants, moisturizers, mouth feel agents, colorants, abrasives, preservatives, fluoride ion source, saliva stimulating agents, emollients, viscosity modifiers, diluents, emulsifiers, nutrients and combinations thereof. Various components that may be added to the oral composition include, for example, a sweetening agent such as saccharin, or sodium saccharin, alcohols such as ethanol, fluoride ion sources such as sodium fluoride, as well as glycerin, sorbitol, polyethylene glycols, Poloxamer polymers such as POLOXAMER® 407, PLURONIC® F108, (both available from BASF Corporation), alkyl polyglycoside (APG), polysorbate, PEG40, castor oil, menthol, and the like. It is understood that while general attributes of each of the above categories of materials may differ, there may be some common attributes and any given material may serve multiple purposes within two or more of such categories of materials. Preferably, such carrier materials are selected for compatibility with the active ingredients found in magnolia extract or synthetic analogues thereof, as well as with other ingredients of the composition.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of 0.01% to 5%, optionally in various embodiments from 0.05 to 2%, from 0.1% to 2.5%, and from 0.1 to 0.5%.

Sweetening agents among those useful herein include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition of the invention.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of 0.001% to 20%, for example 0.01% to 10% or 0.1% to 5%.

In some embodiments, the oral care compositions of the present invention may comprise an optional abrasive useful for example as a polishing agent. Any orally acceptable abrasive can be used, but type, fineness, (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

In some embodiments, the compositions of the present invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

In other embodiments, the oral compositions of the present invention optionally comprise a fluoride ion source, useful, for example, as an anti-caries agent. Any orally acceptable fluoride ion source can be used, including potassium, sodium and ammonium fluorides and monofluorophosphates, stannous fluoride, indium fluoride, amine fluorides such as olaflur (N'-octadecyltrimethylendiamine-N,N, N'-tris(2-ethanol)-dihydrofluoride), and mixtures thereof. One or more fluoride ion sources are optionally present in an amount providing a clinically efficacious amount of soluble fluoride ion to the oral composition.

In further embodiments, the oral compositions of the present invention optionally comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

In yet other embodiments, the oral compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

In some embodiments, the present invention provides a method of treating conditions associated with the presence of oral bacteria comprising providing an oral composition in accordance with any of the above-described embodiments, and applying the oral composition to the oral cavity of the mammalian subject. In some embodiments, the method comprises repeating the application of the composition multiple times until the desired anti-bacterial and/or anti-inflammatory effects are achieved in the subject.

As referred to herein, "inflammation" of the oral tissue generally refers to a localized protective response elicited by injury or destruction of tissues, which serves to destroy, dilute, or sequester both the injurious agent and the injured tissue. In the acute form, it is characterized by pain, heat, redness, swelling, and loss of function. Chronic inflammation is a slow process and primarily characterized by the formation of new connective tissue. Chronic inflammation is often a continuation of acute inflammation or a prolonged low-grade form of inflammation (such as that associated with periodontitis or gingivitis) and usually causes permanent tissue damage. Histologically, inflammation involves a complex series of events, including dilation of arterioles, capillaries, and venules, with increased permeability and blood flow; exudation of fluids, including plasma proteins, and leukocytic migration into the inflammatory locus. Inflammation corresponds to enhanced levels of proinflammatory cellular mediators, or substances that are released from cells, for example, as the result of the interaction of an antigen with an antibody or by the action of antigen with a sensitized lymphocyte.

In various embodiments, application or contacting is accomplished by rinsing, coating, brushing, or layering using appropriate dressing materials. In some embodiments, contacting also includes incidental contact during eating or chewing. In various embodiments, application of the composition comprises the use of an application device which aids in maintaining the contact time of the anti-inflammatory active ingredient comprising isopropyl magnolol to the target tissue for a sufficient time as to allow the pharmacological inhibition of the elevated production of one or more inflammatory mediators, such as PGE 2 and TNF-alpha.

In certain embodiments, an oral composition is not intentionally swallowed, but rather is retained in the oral cavity for a time sufficient to effect the intended utility. In other embodiments, particularly those where the oral composition is provided in an animal product, such as a pet food, pet food supplement (e.g., a treat), or a chew toy, the oral composition may be ingested at small concentrations which are not harmful to the animal. Preferably, specific materials and compositions to be used in this invention are pharmaceutically- or cosmetically-acceptable.

As used throughout, ranges are used as shorthand for describing each and every value that is within the range. Any value within the range can be selected as the terminus of the range.

In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Embodiments of the present invention are further described in the following examples. The examples are merely illustrative and do not in any way limit the scope of the invention as described and claimed.

EXAMPLES

Example 1

A dentifrice is prepared according to the ingredient list provided in Table 1 (below)

TABLE 1

| Ingredient | w/w % |
| --- | --- |
| PEG600 | 3.0 |
| Flavor | 1.0 |
| Isopropyl magnolol (IPM) | 1 |
| Titanium dioxide | 0.5 |
| Sodium CMC | 1.1 |
| Propylene glycol monocaprylate | 1.0 |
| Silica | 21.5 |
| Glycerin | 18 |
| Sorbitol | 17.8 |
| Sodium Saccharine | 0.3 |
| Xanthan gum | 0.4 |
| Sodium Fluoride | 0.243 |
| Sodium lauryl sulfate (SLS) | 1.8 |
| Water | QS |

Example 2

Slurries of 1:2 (dentifrice:water) are prepared. The slurries are centrifuged at 10 k RPM for 10 minutes to separate any undissolved IPM. The supernatants are collected and analyzed for IPM. Table 2 (below) describes the results of the analysis.

TABLE 2

| | Formulations | | | | | |
| --- | --- | --- | --- | --- | --- | --- |
| Ingredient | 1 | 2 | 3 | 1P | 2P | 3P |
| PEG600 | 3 | 3 | 3 | 2 | 2 | 2 |
| PGC | — | — | — | 1 | 1 | 1 |
| Flavor | 1 | 1 | 1 | 1 | 1 | 1 |
| Isopropyl magnolol | 0.5 | 0.7 | 1 | 0.5 | 0.7 | 1 |
| Glycerin | 18 | 18 | 18 | 18 | 18 | 18 |
| Sorbitol (70% solution) | 17.8 | 17.8 | 17.8 | 17.8 | 17.8 | 17.8 |
| Titanium dioxide | 0.5 | 0.5 | 0.5 | 0.5 | 0.5 | 0.5 |
| Sodium fluoride | 0.243 | 0.243 | 0.243 | 0.243 | 0.243 | 0.243 |
| Sodium saccharin | 0.3 | 0.3 | 0.3 | 0.3 | 0.3 | 0.3 |
| Xanthan gum | 0.4 | 0.4 | 0.4 | 0.4 | 0.4 | 0.4 |
| Sodium CMC | 1.1 | 1.1 | 1.1 | 1.1 | 1.1 | 1.1 |
| Silica | 21.5 | 21.5 | 21.5 | 21.5 | 21.5 | 21.5 |
| Sodium lauryl sulfate | 1.8 | 1.8 | 1.8 | 1.8 | 1.8 | 1.8 |
| Water | QS | QS | QS | QS | QS | QS |
| % Solubilized IPM | 0.29 | 0.27 | 0.19 | 0.40 | 0.48 | 0.39 |

Example 3

Anti-inflammatory activity of IPM is evaluated using the Mat Tek $PGE_2$ tissue model.

One (1) mL of tissue culture media (supplied by MatTek) is added to each well of a 6-well plate (×4). The plate is incubated overnight (37° C., 5% $CO_2$). Treatment solutions comprising the dentifrice slurries are prepared, wherein the base dentifrice contains 1% isopropyl magnolol. Slurries of the dentifrices are prepared in a 1:4 ratio by weight of dentifrice:phosphate buffered saline (PBS). Slurries are placed on a stir plate for a minimum of 30 minutes to allow the solution to fully homogenize.

The tissue media is prepared by adding IL-β from a frozen stock solution to the tissue culture media. The final concentration of IL-β in the media is about 10 ng/ml.

1 ml of tissue culture media containing IL-β is added to each well of a 6-well plate (×4). 100 ml of treatment solution is then added to the surface of the tissue and let sit for 2 minutes. The treatment solution is removed by aspiration.

The tissue is then washed using about 200 µl of PBS. PBS is then removed by aspiration, and the process is repeated for a total of 3 washes.

Tissue is then transferred the original 6-well plates to new 6-well plates with media containing IL-β. The plates are incubated (37° C., 5% $CO_2$) for between 7 and 24 hours, depending on the active or dentifrice being tested.

The used media from the old 6-well plates is pipetted into a single 24-well plate, for use as a baseline sample. The plates are removed from the incubator and the used media is pipetted from the 6-well plates into a single 24-well plate, for use as a reference sample for the designated time point. The results of this assay are described in Table 3 (below).

TABLE 3

|  | Butyl magnolol | Isopropyl magnolol | Magnolol | Placebo |
| --- | --- | --- | --- | --- |
| $PGE_2$ reduction (%) | 29.98 | 90.88 | 88.23 | 21.79 |

Example 4

Minimum Inhibitory Concentration (MIC) values are determined generally according to the following method: A series of two-fold dilutions in trypticase soy broth (Catalog No. 211768; Becton Dickinson, Franklin Lakes N.J.) are prepared in a 96 well plate and a constant amount of bacteria is then added to each well. After 18-24 hours of incubation, bacterial growth is measured with a Spectrophotometric Micro-plate Reader (Powerwave 5x, BioTEK, Winooski Vt.) and the MIC values are determined.

Table 4 (below) describes the antibacterial efficacy of isopropyl magnolol against various oral pathogens.

TABLE 4

|  | MIC (ppm) | |
| --- | --- | --- |
| Species | Magnolol | Isopropyl magnolol |
| *A. actinomycetemcomitans* | 15.6 | 3.9 |
| *Streptococcus sanguis* | 15.6 | 1.95 |
| *Streptoccus mutans* | 15.6 | 3.9 |

TABLE 4-continued

|  | MIC (ppm) | |
| --- | --- | --- |
| Species | Magnolol | Isopropyl magnolol |
| *Fusobcaterium nucleatum* | 7.8 | 0.97 |
| *Actinomyces viscosus* | 15.6 | 3.9 |

Example 5

Hydroxyapatite (HAP) disks are pre-treated with clarified saliva overnight. After aspiration of the saliva, the disks are treated with 1 mL of 1:2 (paste:water) slurry for 2 minutes at 37 deg. Celsius. The slurry is aspirated and the disks are rinsed three times with 5 mL of DI water for 10 seconds. The active is extracted with 1 mL of ethyl alcohol for 2 hours and then analyzed by HPLC. The results are described in Table 5 (below).

TABLE 5

| Sample | Formula Notes | Conc (µg/disc) | Avg | Std Dev |
| --- | --- | --- | --- | --- |
| A | 1% IPM, 1% PG-caprylate, 2% PEG600, 1.5% SLS | 6.60 7.05 7.48 | 7.04 | 0.44 |
| B | 1% IPM, 1% PG-laurate, 2% PEG600, 1.5% SLS | 3.14 5.39 6.05 | 4.86 | 1.53 |

The invention claimed is:

1. An oral care composition comprising:
   isopropyl magnolol;
   an orally acceptable carrier; and
   a surfactant system, wherein the surfactant system comprises a surfactant having an HLB value greater than 10 and a co-surfactant having an HLB value of less than about 10, the isopropyl magnolol is present in the amount of from about 0.1% to about 3% based on the total weight of the composition, the ratio by weight of isopropyl magnolol to the co-surfactant is from about 0.1:1 to about 2:1, the surfactant having an HLB value greater than 10 is sodium lauryl sulfate and the co-surfactant is propylene glycol monocaprylate.

2. The composition of claim 1, wherein the co-surfactant is present in an amount sufficient to solubilize the isopropyl magnolol in the orally acceptable carrier.

3. The composition of claim 1, in the form of a toothpaste.

4. The composition of claim 1, in the form of a mouthrinse.

5. A method of treating a disease or condition of the oral cavity, comprising administering a composition according to claim 1, to the oral cavity of a subject in need thereof.

6. The method of claim 5, wherein the disease or condition of the oral cavity is selected from caries, gingivitis, periodontitis, tooth yellowing and halitosis.

* * * * *